(12) United States Patent
Maskara et al.

(10) Patent No.: US 9,320,906 B2
(45) Date of Patent: Apr. 26, 2016

(54) HEART SOUNDS TEMPLATE COMPARISON TO IDENTIFY TRUE PACING MODE

(71) Applicant: Cardiac Pacemakers, Inc., St. Paul, MN (US)

(72) Inventors: Barun Maskara, Blaine, MN (US); Qi An, Blaine, MN (US); Pramodsingh Hirasingh Thakur, Woodbury, MN (US); Julie A. Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/187,954

(22) Filed: Feb. 24, 2014

(65) Prior Publication Data

US 2014/0277243 A1     Sep. 18, 2014

Related U.S. Application Data

(60) Provisional application No. 61/776,941, filed on Mar. 12, 2013.

(51) Int. Cl.
*A61N 1/37* (2006.01)
*A61N 1/368* (2006.01)
*A61N 1/362* (2006.01)
*A61N 1/365* (2006.01)

(52) U.S. Cl.
CPC .............. *A61N 1/371* (2013.01); *A61N 1/3627* (2013.01); *A61N 1/3684* (2013.01); *A61N 1/36578* (2013.01)

(58) Field of Classification Search
USPC ................................ 607/4, 9, 17, 28; 600/513
See application file for complete search history.

(56) References Cited

U.S. PATENT DOCUMENTS

| 6,650,940 | B1 | 11/2003 | Zhu et al. |
| 7,899,536 | B1 | 3/2011 | Hellman |
| 2006/0155338 | A1* | 7/2006 | Mongeon et al. ................ 607/9 |
| 2008/0269825 | A1 | 10/2008 | Chinchoy et al. |
| 2010/0198284 | A1* | 8/2010 | Zhou et al. ........................ 607/4 |
| 2011/0077543 | A1 | 3/2011 | Patangay et al. |
| 2012/0296228 | A1* | 11/2012 | Zhang et al. ................ 600/513 |

FOREIGN PATENT DOCUMENTS

WO    WO-2014163844 A1    10/2014

OTHER PUBLICATIONS

"International Application Serial No. PCT/US2014/017993, International Search Report mailed May 9, 2014", 5 pgs.
"International Application Serial No. PCT/US2014/017993, Written Opinion mailed May 9, 2014", 7 pgs.
"International Application Serial No. PCT/US2014/017993, International Preliminary Report on Patentability mailed Sep. 24, 2015", 9 pgs.

* cited by examiner

*Primary Examiner* — Carl H Layno
*Assistant Examiner* — Jon Eric C Morales
(74) *Attorney, Agent, or Firm* — Schwegman Lundberg & Woessner, P.A.

(57) ABSTRACT

An apparatus may include an implantable therapy circuit that provides bi-ventricular pacing to a subject, a heart sound signal sensing circuit that produces a sensed heart sound signal that is representative of at least one heart sound associated with mechanical cardiac activity, a memory circuit to store one or more heart sound templates of cardiac capture, and a comparison circuit that compares a segment of the sensed heart sound signal to the one or more heart sound templates of cardiac capture to identify ventricles in which cardiac capture was induced by the bi-ventricular pacing. In some situations, an indication of the ventricles in which cardiac capture was induced may be generated according to the comparison.

20 Claims, 3 Drawing Sheets

HEART SOUNDS TEMPLATE COMPARISON TO IDENTIFY TRUE PACING MODE

CLAIM OF PRIORITY

This application claims the benefit of U.S. Provisional Patent Application Ser. No. 61/776,941, filed on Mar. 12, 2013, the benefit of priority of which is claimed hereby, and which is incorporated by reference herein in its entirety.

BACKGROUND

Ambulatory medical devices include implantable medical devices (IMDs) and wearable medical devices. Some examples of IMDs include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. The devices may be implanted subcutaneously and include electrodes that are able to sense cardiac signals without being in direct contact with the patient's heart. Other examples of IMDs include implantable diagnostic devices, implantable drug delivery systems, or implantable devices with neural stimulation capability.

Some examples of wearable medical devices include wearable cardioverter defibrillators (WCDs) and wearable diagnostic devices (e.g., an ambulatory monitoring vest). WCDs can be monitoring devices that include surface electrodes. The surface electrodes are arranged to provide one or both of monitoring to provide surface electrocardiograms (ECGs) and delivering cardioverter and defibrillator shock therapy.

In response to an abnormally slow heart rate or lack of coordination among contraction of the ventricles, some CFM devices deliver electrical pacing stimulation to induce cardiac depolarization and contraction (sometimes referred to as capture of the heart). It is desirable for a physician to know the effectiveness of the pacing stimulation therapy provided to the subject. A system and method for monitoring at least one chamber of a heart during delivery of refractory period stimulation to determine if desired non-capture occurs can be found in Chinchoy et al., "Mechanical Ventricular Pacing Non-Capture Detection for a Refractory Period Stimulation (RPS) Pacing Therapy Using at Least One Lead-Based Accelerometer," U.S. Patent Application Publication No. US 2008/0269825, filed Apr. 30, 2007. An implantable cardiac rhythm management device capable of automatically detecting intrinsic evoked response of a patient's heart can be found in Zhu et al., Accelerometer-Based Heart Sound Detection for Autocapture," U.S. Pat. No. 6,650,940, filed Feb. 2, 2008.

Overview

This document discusses systems, devices and methods for improved determination of efficacy of cardiac therapy for a patient or subject. An apparatus example can include an implantable therapy circuit configured to provide bi-ventricular pacing to a subject, a heart sound signal sensing circuit configured to produce a sensed heart sound signal that is representative of at least one heart sound associated with mechanical cardiac activity, a memory circuit configured to store one or more heart sound templates of cardiac capture, and a comparison circuit configured to compare a segment of the sensed heart sound signal to the one or more heart sound templates of cardiac capture to identify ventricles in which cardiac capture was induced by the bi-ventricular pacing and generate an indication of the ventricles in which cardiac capture was induced according to the comparison and providing the indication to at least one of a user or process.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An ambulatory medical device may include one or more of the features, structures, methods, or combinations thereof described herein. For example, an ambulatory cardiac monitor or cardiac stimulator may be implemented to include one or more of the advantageous features or processes described below. It is intended that such a monitor, stimulator, or other implantable, partially implantable, or wearable device need not include all of the features described herein, but may be implemented to include selected features that provide for unique structures or functionality. Such a device may be implemented to provide a variety of therapeutic or diagnostic functions.

Figure 1:
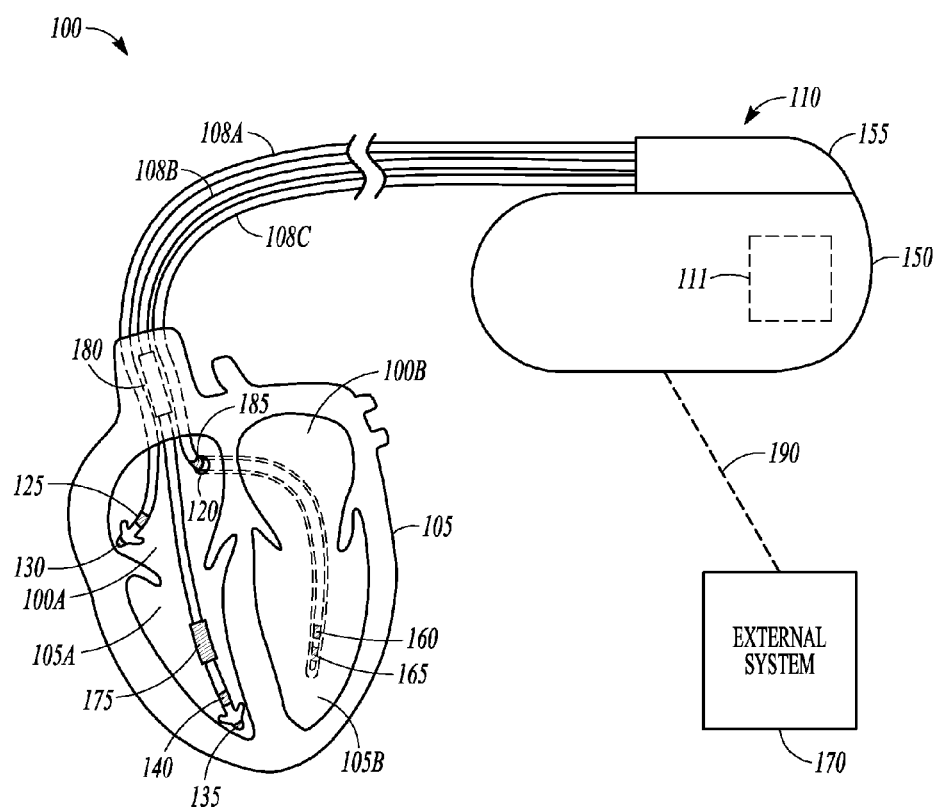
FIG. 1 is an illustration of portions of a system that uses an ambulatory medical device that is an IMD.

FIG. 1 is an illustration of portions of a system that uses an ambulatory medical device that is an IMD 110. Examples of IMD 110 include, without limitation, a pacer, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals. The external device 170 may communicate with a remote system via a network, such as a computer network or cellular phone network. In some examples, the remote system provides patient management functions and may include one or more servers to perform the functions.

The IMD 110 is shown coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 may include a third cardiac lead 108C attached to the IMD 110 through the header 155. The third cardiac lead 108C includes electrodes 160 and 165 placed in a coronary vein lying epicardially on the left ventricle (LV) 105B via the coronary vein. The third cardiac lead 108C may include a ring electrode 185 positioned near the coronary sinus (CS) 120. Although only two electrodes are shown in the example of the Figure, lead 108C may include three electrodes, four electrodes, or any number of electrodes as desired.

Lead 108B may include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown in the illustration, the present methods and systems will work in a variety of configurations and with a variety of electrodes. An IMD may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

The IMD 110 can also include a heart signal sensing circuit 111. The heart sound signal sensing circuit 111 may be configured to produce a sensed heart sound signal that is representative of at least one heart sound associated with mechanical cardiac activity of a subject. Some examples of a heart sound signal sensing circuit 111 can include an accelerometer, a microphone, or other suitable heart sound sensor.

Figure 2:
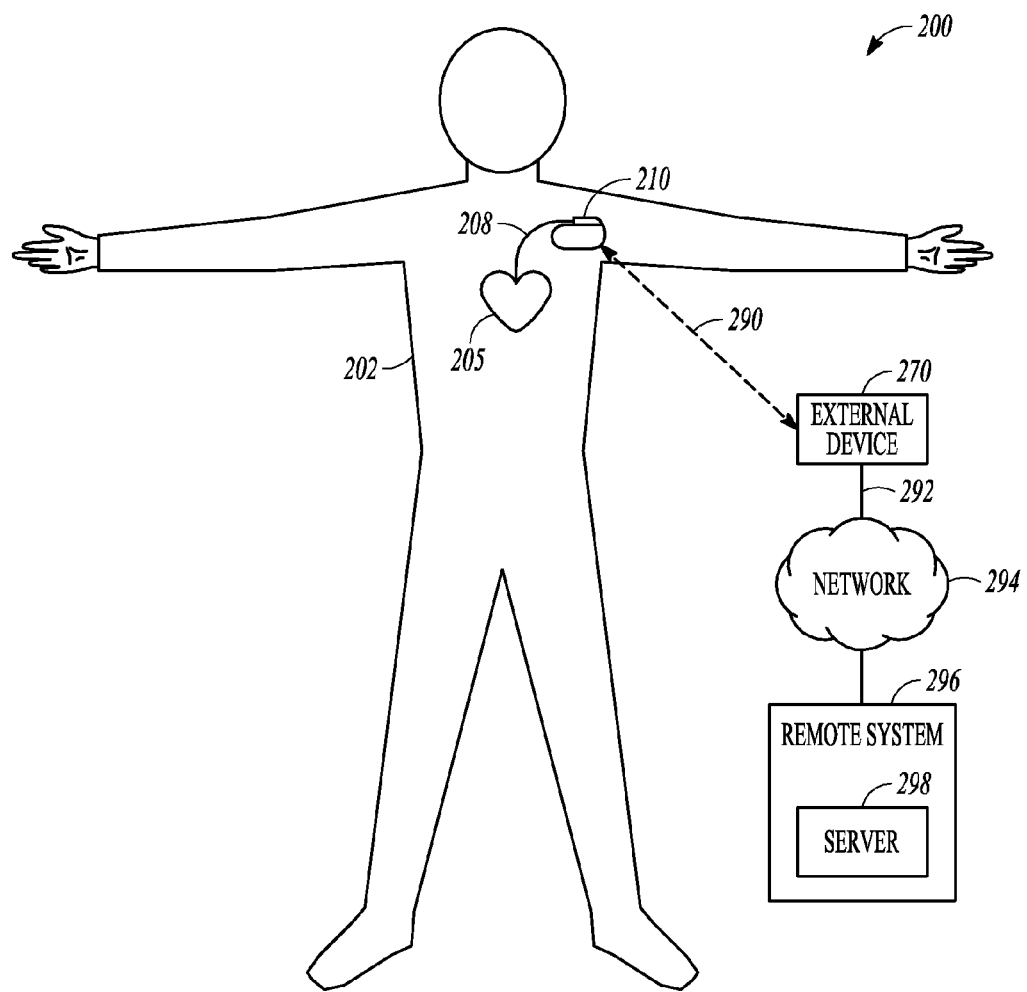
FIG. 2 is an illustration of portions of another system that uses an IMD to provide a therapy to a patient.

FIG. 2 is an illustration of portions of another system 200 that uses an IMD 210 to provide a therapy to a patient 202. The system 200 typically includes an external device 270 that communicates with a remote system 296 via a network 294. The network 294 can be a communication network such as a phone network or a computer network (e.g., the internet). In some examples, the external device 270 includes a repeater and communicates via the network using a link 292 that may be wired or wireless. In some examples, the remote system 296 provides patient management functions and may include one or more servers 298 to perform the functions.

The IMD may track what therapy was provided to a patient or subject according to whether the device delivered a pacing pulse to a particular heart chamber of the subject. For example, counters may be used by the device to track bi-ventricular or bi-V pacing stimulation pulses provided. However, in some situations, device-based counters may inaccurately estimate the degree of bi-V pacing that effectively captures the heart. This can be especially true if the device is estimating effective pacing therapy during an episode of atrial fibrillation (AF) experienced by the subject. The actual degree of bi-V pacing that is effective may be lower than an estimate of bi-V pacing delivered determined using device counters. Also, a fusion beat can occur when a device delivers a pacing pulse to a ventricle, but the majority of the ventricle is still activated through intrinsic depolarization. The occurrence of fusion beats can impact the accuracy of the estimate of effective bi-V pacing when using device counters.

Heart sounds are associated with mechanical cardiac activity. This is in contrast to electrical cardiac activity that is associated with electrical action potentials due to cardiac depolarization. A "heart sound" can include a first heart sound (S1), a second heart sound (S2), a third heart sound (S3), a fourth heart sound (S4), or any components thereof, such as the aortic component of S2 (A2), the pulmonary component of S2 (P2), or other broadband sounds or vibrations associated with mechanical activity of the heart, such as valve closures or fluid movement (e.g., a heart murmur, etc.). Heart sounds can also include one or more broadband chest sounds, such as may result from one or more of mitral regurgitation, left ventricle dilation, etc.

Sensing heart sounds can be used to determine if a pacing stimulation pulse induced an evoked response or cardiac capture of the heart. Only sensing electrical signals may provide an indication of an electrical action potential traversing a region of the heart as the result of a pacing stimulation pulse, but may not provide an indication that the action potential induced a mechanical contraction. Heart sounds can be used, with or without device counters, to discriminate effective capture of the left ventricle (LV), right ventricle (RV), or both ventricles from no capture or inadequate capture of the ventricles.

Figure 3:
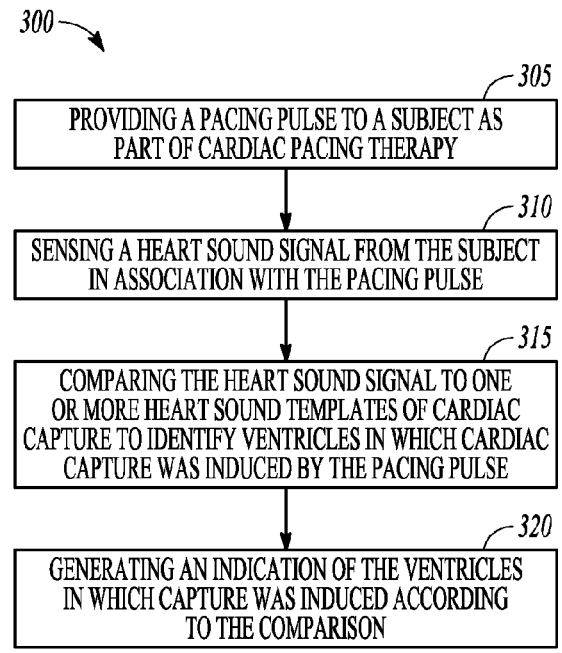
FIG. 3 shows a flow diagram of an example of a method of determining effective cardiac pacing therapy.

FIG. 3 shows a flow diagram of an example of a method 300 of determining effective cardiac pacing therapy. At block 305, a bi-ventricular (bi-V) pacing pulse is provided to the subject by an ambulatory medical device as part of cardiac pacing therapy (e.g., CRT). In certain examples, the ambulatory medical device is an implantable medical device. The bi-V pacing pulse includes an electrical pacing stimulation pulse delivered to the RV and an electrical stimulation pulse delivered to the LV.

At block 310, a heart sound signal is sensed by the device in association with providing the bi-V pacing pulse. Characteristics or attributes of the sensed heart sound signal can indicate whether or not capture occurred in one or both of the ventricles. One method for device-based identification of capture in heart sound signals is using template comparisons.

A template can represent a segment of a sensed heart sound signal. In some examples, multiple heart sound signals are sensed and a central tendency (e.g., an average) of the heart sound signals can be used as the template. Using a central tendency of the signal can help to remove or reduce noise from the template. The one or more sensed heart sound signals can be compared to one or more heart sound templates representative of RV capture only, LV capture only, and capture in both ventricles (bi-V capture), to determine an assessment of capture resulting from the pacing stimulation.

At block 315, a segment of the sensed heart sound signal can be compared to one or more heart sound templates indicative of cardiac capture (e.g., RV capture, LV capture, or bi-V capture). In this way, the ventricles can be identified in which capture was induced by the bi-V pacing pulse. At block 320, an indication of those ventricles in which capture was induced can be generated and provided to at least one of a user, physician, or process. Because confirmation of capture is determined using the heart sound signal, the method may provide a more accurate determination of the degree of bi-V pacing therapy that is effectively delivered.

Figure 4:
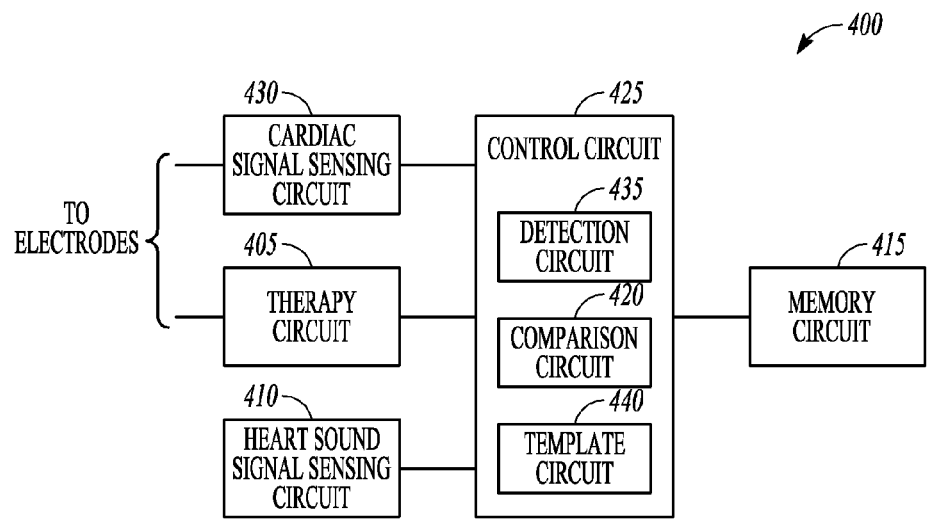
FIG. 4 is block diagram of portions of an example of an ambulatory medical device that determines the efficacy of cardiac pacing therapy provided to a subject.

FIG. 4 is block diagram of portions of an example of an ambulatory medical device 400 that determines the efficacy of cardiac pacing therapy provided to a subject. The device includes an implantable therapy circuit 405 that provides a bi-V pacing pulse to the subject as part of cardiac pacing therapy. The cardiac pacing therapy can include CRT or bradycardia pacing therapy.

The device also includes a heart sound signal sensing circuit 410 and a memory circuit 415. The heart sound signal sensing circuit 410 produces a sensed heart sound signal representative of at least one heart sound. The heart sound is associated with mechanical activity of the heart of the subject, as discussed previously. The memory circuit 415 can be configured to store one or more heart sound templates that are representative of a heart sound signal sensed during cardiac capture. For example, the memory circuit 415 may be configured to store a RV capture template, a LV capture template, a bi-V capture template, a template of intrinsic an heat beat, and combinations thereof.

The ambulatory medical device 400 may further includes a comparison circuit 420 in electrical communication with the heart sound signal sensing circuit 410 and the memory circuit 415. The electrical communication allows electrical signals to be communicated between the comparison circuit 420 and the heart sound signal sensing circuit 410 and the memory circuit 415 even though there may be intervening circuits between the comparison circuit 420 and the heart sound signal sensing circuit 410 and the memory circuit 415. The comparison circuit 420 can be configured to compare at least a segment of the sensed heart sound signal to the one or more heart sound templates representative of cardiac capture. For example, the comparison circuit 420 may be configured to calculate a coefficient of correlation for at least one or more templates based on the comparison. The coefficient of correlation may provide a metric of how well the sensed signal correlates with the specific heart sound template. The sensed heart sound signal may be determined to be representative of the template when the calculated coefficient of correlation exceeds a threshold coefficient value. In some cases, the threshold coefficient value can be specified or programmed by the device manufacturer or a user (e.g., a physician). In some cases, the sensed heart sound signal may be determined to be representative of one of the one or more templates when the calculated correlation coefficient corresponding to the template has the highest value among all the calculated correlation coefficients.

The comparison circuit 420 may be included in a control circuit 425. The control circuit 425 can be a microprocessor, a digital signal processor, application specific integrated circuit (ASIC), microprocessor, or other type of processor, interpreting or executing instructions in software modules or firmware modules. The control circuit 425 can include other circuits or sub-circuits to perform the functions described. These circuits may include software, hardware, firmware or any combination thereof. Multiple functions can be performed in one or more of the circuits as desired.

The comparison circuit 420 can be configured to compare the segment of the sensed heart sound signal to one or more heart sound signal templates to identify ventricles in which cardiac capture was induced by the bi-ventricular pacing pulse. The one or more heart sound signal templates may be representative of at least one of a heart sound signal sensed during pacing of only a RV, a heart sound signal sensed during pacing of only a LV, a heart sound signal sensed during bi-V pacing, or a heart sound signal representative of ventricular contraction resulting from intrinsic depolarization. To obtain the heart sound signal segment, the sensing of the heart sound signal can be gated or triggered by delivery of the pacing pulse. In another example, the segment of the sensed heart sound signal can be identified by algorithmically determining a heart sound (e.g., the S1 heart sound) in the sensed heart sound signal.

In some examples, the comparison circuit 420 can be configured to generate an indication of the ventricle or ventricles in which capture was induced according to the comparison, or generates an indication of no capture according to the comparison. The indication can be provided to a user or a process. In some examples, the device includes one or more counters. The indication generated by the comparison circuit 420 can be used to update one or more of a count of capture induced in the RV only by the bi-V pacing pulse, a count of capture induced in the LV only, a count of capture induced in both ventricles, and a count of lack of capture induced in the ventricles by the bi-V pace pulse. It should be noted that this is different than merely counting in which heart chamber a pace pule was delivered because effectiveness or ineffectiveness of the pace pulse is confirmed using heart sounds.

In certain examples, the heart sound signal sensing circuit 410 senses a heart sound signal that includes at least a portion of a sensed S1 heart sound. The comparison circuit 420 compares a segment of the sensed heart sound signal that includes at least the portion of the S1 heart sound to one or more templates representative of an S1 heart sound. The S1 templates can be representative of one or both of capture and non-capture, and the indication can be generated by the comparison circuit 420 according to the result of the comparison. Using a comparison of the S1 heart sound to templates representative of RV capture only, LV capture only, bi-V capture, and intrinsic cardiac depolarization can provide an indication of capture of the ventricles.

In some examples, the device includes a cardiac signal sensing circuit 430 and a detection circuit 435. The cardiac signal sensing circuit 430 can be configured to provide a sensed cardiac signal representative of electrical cardiac activity of the subject. Some examples of a cardiac signal sensing circuit are a sense amplifier in electrical communication with implantable electrodes or with surface electrodes. The cardiac signal may be sensed as an electrogram or an electrocardiogram. The detection circuit 435 can be configured to detect an episode of AF using the sensed cardiac signal. In certain examples, the detection circuit 435 can include a heart rate detection circuit and detects AF using a detected atrial depolarization rate. The control circuit 425 can initiate delivery of one or more bi-V pacing pulses during the detected episode of AF. The comparison circuit 420 may generate an indication of the ventricles in which capture was induced by one or more bi-V pacing pulses provided during the detected episode of AF. The device may include separate counters to specifically track counts for events detected during AF.

In some examples, the comparison circuit 420 can be configured to scale a heart sound template in as a function of detected heart rate. The heart sound templates representative of cardiac capture can be scaled in one or both of time and amplitude. For instance, a heart sound template could be scaled in one or both of amplitude (e.g., by shrinking or expanding the template signal along the y-axis) and time (e.g., shrinking or expanding the template signal along x-axis) as a function of heart rate. At a higher high rate, it may be expected for the S1 heart sound to be louder (therefore the amplitude of the signal may be scaled up) and also since the cardiac cycle is shortened when the rate is higher, the duration of S1 may be shorter (therefore the template signal may be scaled shorter in time). Hence, the comparison circuit 420 may scale the heart sound template used in the comparison according to the sensed heart rate.

The device 400 may generate its own templates for use by the comparison circuit 420 in the comparisons. According to some examples, the device includes a template circuit 440. The template circuit 440 may generate heart sound templates representative of cardiac capture in the RV, in the LV, in both ventricles, and heart sound templates representative of ventricular contraction resulting from an intrinsic depolarization.

In some examples, the control circuit 425 can be configured to initiate a template mode to generate a heart sound template. In the template mode, one or more electrical stimulation pulses are delivered to one or both ventricles according to the kind of template of interest (e.g., RV only, LV only, bi-V), or delivery of pacing pulses can be suspended if the template of interest is for intrinsic heart beats. The electrical stimulation pulses may be provided using a stimulation interval that is less than a shortest detected intrinsic depolarization interval and may have a high enough amplitude to ensure capture by the pulses. In certain examples, the shortest interval detected over a specified number of previous cardiac cycles is used as the shortest interval. Pacing at an interval that is less than a shortest intrinsic interval is useful to avoid the presence of intrinsic fusion beats in the heart sound signal or signals used to generate a heart sound template. In this way, separate templates can be constructed for true RV only heart beats, true LV only heart beats, and true bi-V heart beats. A separate template can also be generated for true intrinsic beats by suspending pacing altogether for a specified number of intrinsic beats. Once heart sound templates are formed, the device can chronically monitor heart beats and compare the heat sound features to the templates to correctly classify heartbeats based on a calculated similarity to, or difference from, the four types of heart sound templates.

In some examples, the control circuit 425 can be configured to initiate the generation of heart sound templates in a confirmation mode. In confirmation mode, the template circuit 440 generates a candidate heart sound template representative of cardiac capture in the RV only, cardiac capture in the LV only, or cardiac capture in both ventricles using heart sound signals sensed during pacing of the RV only, the LV only, or both ventricles, respectively. The template circuit 440 may also generate a candidate heart sound template corresponding to ventricular contraction resulting from intrinsic depolarization. When a candidate template is obtained, the control circuit 425 may cause the template to be communicated to a second device (e.g., by inductive or radio frequency telemetry) for presentation (e.g., display) to a user. After inspecting the candidate template, the user may enter an indication of acceptance of the candidate template for use in detecting cardiac capture, such as by entering the indication into the second device via a user interface for example. The second device may then communicate the indication to the control circuit 425.

Upon receiving the indication of acceptance of the candidate heart sound template, the control circuit may classify the candidate heart sound template as usable in a comparison to segment of a sensed heart sound signal. The classification may include storing the candidate template in a different area of memory reserved for templates that have been accepted by a user, or may include setting a flag or other indicator that the candidate template has been accepted by a user. The control circuit 425 may then initiate a comparison of a segment of a sensed heart sound signal to the candidate template as a result of one or both of the received indication of acceptance and the re-classification of the candidate template. If the template is not accepted, it may be discarded.

In some examples, the control circuit 425 can be configured to initiate the generation of heart sound templates in an automatic mode. In automatic mode, similar to the confirmation mode, the template circuit 440 generates a candidate heart sound template representative of cardiac capture in the RV only, cardiac capture in the LV only, or cardiac capture in both ventricles using heart sound signals sensed during pacing of the RV only, the LV only, or both ventricles, respectively.

When a candidate template is generated, the template circuit calculates a metric of separation of the candidate heart sound template from a heart sound template representative of ventricular contraction resulting from intrinsic depolarization. The heart sound template associated with intrinsic depolarization may also have been generated by the template circuit 440 by suspending pacing stimulation for a specified number of cardiac cycles. Based on the calculated metric, the control circuit 425 may classify the candidate heart sound template as usable in a subsequent comparison to a segment of a sensed heart sound signal, or the candidate template may be discarded.

The control circuit 425 may compare the calculated metric to a metric threshold value, and classify the candidate heart sound template as usable when the calculated metric satisfies the threshold. The classification of the template as usable may include storing the candidate template in a different area of memory reserved for templates that have been accepted by a user, or may include setting a flag or other indicator that the candidate template has been accepted by a user. The control circuit 425 may then initiate a comparison of a segment of a sensed heart sound signal to the candidate template that has been classified as usable. The process may be repeated multiple times by the device and templates with heart sound features having the greatest degree of separation from the intrinsic heart sound features can be selected as templates for a given mode of pacing.

While the description has focused on bi-V pacing, the methods, devices, and systems described herein can also be applied to other types of pacing such as RV only or LV only to verify capture. For instance, in pacemakers ventricular pacing pulses are typically provided to the RV only and the methods described can be used to distinguish between RV only capture and loss of capture or intrinsic depolarization.

Using heart sounds to determine efficacy of pacing adds a mechanical assessment of the response of the heart to electrical pacing therapy. Knowing the efficacy of the device-based pacing therapy prescribed may assist a physician in optimizing the performance of the device for a specific patient or subject. If the percentage of capture is presented to a physician, this measure can be used to reprogram (e.g., optimize) parameters for CRT. This reprogramming or re-optimizing may include changing the AV delay, the VV delay, a pacing site, and stimulation parameters (e.g., pacing amplitude, pulse width, etc.). The process of re-optimization of parameters may be triggered when the percentage of capture drops below a threshold in order to increase or maximize the efficacy of pacing therapy.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus comprising:
an implantable therapy circuit configured to provide a bi-ventricular pacing pulse to a subject as part of cardiac pacing therapy, wherein the bi-ventricular pacing pulse includes providing an electrical stimulation pulse to a right ventricle and an electrical stimulation pulse to a left ventricle;
a heart sound signal sensing circuit configured to produce a sensed heart sound signal that is representative of at least one heart sound associated with mechanical cardiac activity of a subject;
a memory circuit configured to store one or more heart sound templates of cardiac capture; and
a comparison circuit configured to:
compare a segment of the sensed heart sound signal to a template heart sound signal representative of ventricular contraction resulting from intrinsic depolarization and at least one of a template heart sound signal representative of right ventricle (RV) capture only, a template heart sound signal representative of left ventricle (LV) capture only, and a template heart sound signal representative of bi-ventricular capture;
identify ventricles in which cardiac capture was induced by the bi-ventricular pacing pulse; and
generate an indication of the ventricles in which capture was induced or an indication of no cardiac capture of a ventricle according to the comparison and providing the indication to at least one of a user or process.

2. The apparatus of claim 1, including:
a cardiac signal sensing circuit configured to provide a sensed cardiac signal representative of electrical cardiac activity of the subject;
a detection circuit configured to detect an episode of atrial fibrillation using the sensed cardiac signal; and
a control circuit configured to initiate delivery of one or more bi-ventricular pacing pulses during the detected episode of atrial fibrillation,
wherein the comparison circuit is configured to generate an indication of the ventricles in which capture was induced by one or more bi-ventricular pacing pulses provided during the detected episode of atrial fibrillation.

3. The apparatus of claim 1, wherein the comparison circuit is configured to compare the segment of the sensed heart sound signal to at least one of a template heart sound signal representative of a heart sound signal sensed during pacing of only a right ventricle (RV), a template heart sound signal representative of a heart sound signal sensed during pacing of only a left ventricle (LV), a template heart sound signal representative of a heart sound signal sensed during bi-ventricular pacing, and a template heart sound signal representative of ventricular contraction resulting from intrinsic depolarization; and generate the indication of the ventricles in which capture was induced or an indication of no cardiac capture according to the comparison.

4. The apparatus of claim 1, wherein the heart sound signal sensing circuit is configured to sense a heart sound signal that includes at least a portion of a sensed S1 heart sound, and wherein the comparison circuit is configured to compare a segment of the sensed heart sound signal that includes the at least a portion of a sensed S1 heart sound to one or more templates representative of an S1 heart sound.

5. The apparatus of claim 1, wherein the comparison circuit is configured to generate an indication that up dates, according to the comparison, a count of capture induced in the RV only, a count of capture induced in the LV only, a count of capture induced in both ventricles, and a count of lack of capture in the ventricles.

6. The apparatus of claim 1, including a template circuit configured to generate heart sound templates representative of cardiac capture in the RV, in the LV, and in both ventricles, and generating a heart sound template representative of ventricular contraction due to intrinsic depolarization.

7. The apparatus of claim 6, including a control circuit configured to initiate a template mode in which one or more electrical stimulation pulses are delivered to one or both ventricles, wherein the electrical stimulation pulses are provided using a stimulation interval that is less than a shortest detected intrinsic depolarization interval, and wherein the template circuit is configured to generate a heart sound template using one or more heart sound signals sensed when providing the one or more electrical stimulation pulses to the one or both ventricles in the template mode.

8. The apparatus of claim 1, including:
a template circuit configured to generate a candidate heart sound template representative of at least one of cardiac capture in the RV only, cardiac capture in the LV only, cardiac capture in both ventricles, or representative of ventricular contraction resulting from intrinsic depolarization; and
a control circuit configured to receive an indication of acceptance of the candidate template, and wherein the control circuit is configured to initiate a comparison of a segment of a sensed heart sound signal to the candidate template up on receiving the indication of acceptance of the candidate template.

9. The apparatus of claim 1, including:
a template circuit configured to:
generate a candidate heart sound template representative of cardiac capture resulting from an electrical stimulation pulse delivered to at least one of the RV only, the LV only, or to both ventricles; and
calculate a metric of separation of the candidate heart sound template from a heart sound template representative of ventricular contraction resulting from intrinsic depolarization; and
a control circuit configured to initiate a comparison of a segment of a sensed heart sound signal to the candidate heart sound template according to the calculated metric.

10. The apparatus of claim 1, including a heart rate detection circuit, wherein the comparison circuit is configured to scale the one or more heart sound templates of cardiac capture in one or both of time and amplitude as a function of detected heart rate, wherein compare the segment of the sensed heart sound signal to one or more scaled heart sound templates.

11. A method comprising
providing, to a subject by an implantable device, a bi-ventricular pacing pulse as part of cardiac pacing therapy, wherein the bi-ventricular pacing pulse includes providing an electrical stimulation pulse to a right ventricle and an electrical stimulation pulse to a left ventricle;
sensing a heart sound signal from the subject in association with the bi-ventricular pacing pulse, wherein a heart sound signal is associated with mechanical activity of the heart of the subject;
comparing by the implantable device, a segment of the sensed heart sound signal to a template heart sound signal representative of ventricular contraction resulting from intrinsic depolarization and at least one of a template heart sound signal representative of right ventricle (RV) capture only, a template heart sound signal representative of left ventricle (LV) capture only, and a template heart sound signal representative of bi-ventricular capture;
identifying ventricles in which cardiac capture was induced by the bi-ventricular pacing pulse; and
generating an indication of the ventricles in which capture was induced or an indication of no cardiac capture of a ventricle according to the comparison and providing the indication to at least one of a user or process.

12. The method of claim 11, including detecting, by the implantable device, an episode of atrial fibrillation, wherein providing a bi-ventricular pacing pulse includes providing one or more bi-ventricular pacing pulses during the episode of atrial fibrillation, and wherein the generating an indication includes generating an indication of the ventricles in which capture was induced by the one or more bi-ventricular pacing pulses provided during the episode of atrial fibrillation.

13. The method of claim 11, wherein comparing a segment of the sensed heart sound signal includes comparing the segment of the sensed heart sound signal to at least one of a template heart sound signal representative of a heart sound signal sensed during pacing of only a right ventricle (RV), a template heart sound signal representative of a heart sound signal sensed during pacing of only a left ventricle (LV), a template heart sound signal representative of a heart sound signal sensed during bi-ventricular pacing, and a template heart sound signal representative of ventricular contraction resulting from intrinsic depolarization.

14. The method of claim 11, wherein sensing a heart sound signal includes sensing a heart sound signal that includes at least a portion of a sensed S1 heart sound, and wherein comparing a segment of the sensed heart sound signal includes comparing a segment of the sensed heart sound signal that includes the at least a portion of a sensed S1 heart sound to one or more templates representative of an S1 heart sound.

15. The method of claim 11, wherein generating an indication includes updating, according to the comparison, a count of capture induced in the RV only, a count of capture induced in the LV only, a count of capture induced in both ventricles, and a count of lack of capture in the ventricles.

16. The method of claim 11, including generating, by the implantable device, heart sound templates representative of cardiac capture in the RV, in the LV, and in both ventricles, and generating a heart sound template representative of ventricular contraction due to intrinsic depolarization.

17. The method of claim 16, wherein generating heart sound templates representative of cardiac capture includes generating a heart sound template using one or more heart sound signals sensed when providing electrical stimulation pulses to one or both ventricles using a stimulation interval that is less than a shortest detected intrinsic depolarization interval.

18. The method of claim 11, including:
generating, by the implantable device, a candidate heart sound template representative of at least one of cardiac capture in the RV only, cardiac capture in the LV only, cardiac capture in both ventricles, or ventricular contraction resulting from intrinsic depolarization;
receiving, by the implantable device, an indication of acceptance of the candidate heart sound template; and
classifying the candidate heart sound template as usable in a comparison to a segment of a sensed heart sound signal up on receiving the indication of acceptance of the candidate template.

19. The method of claim 11, including:
generating, by the implantable device, a candidate heart sound template representative of cardiac capture resulting from at least one of a pacing stimulation pulse provided to the RV only, a pacing stimulation pulse provided to the LV only, or a pacing stimulation pulse provided to both ventricles;
calculating a metric of separation of the candidate heart sound template from a heart sound template representative of ventricular contraction resulting from intrinsic depolarization; and
classifying the candidate heart sound template as usable in a comparison to a segment of a sensed heart sound signal according to the calculated metric.

20. The method of claim 11, including:
determining a heart rate of the subject; and
scaling the one or more heart sound templates of cardiac capture in or both of time and amplitude as a function of the determined heart rate, wherein comparing a segment of the sensed heart sound signal includes comparing a segment of the sensed heart sound signal to one or more scaled heart sound templates.

* * * * *